United States Patent
Kidd et al.

(10) Patent No.: US 7,998,020 B2
(45) Date of Patent: Aug. 16, 2011

(54) APPARATUS FOR SELECTIVELY ROTATING AND/OR ADVANCING AN ELONGATE DEVICE

(75) Inventors: Brian Kidd, St. Louis, MO (US); Richard Hitchens, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 192 days.

(21) Appl. No.: 12/328,304

(22) Filed: Dec. 4, 2008

(65) Prior Publication Data

US 2009/0105645 A1  Apr. 23, 2009

Related U.S. Application Data

(63) Continuation-in-part of application No. 12/196,058, filed on Aug. 21, 2008, now abandoned.

(60) Provisional application No. 60/957,008, filed on Aug. 21, 2007.

(51) Int. Cl.
*F16H 15/04* (2006.01)
*F16H 37/00* (2006.01)
*A61M 25/00* (2006.01)

(52) U.S. Cl. .............................. 476/19; 476/34; 604/528
(58) Field of Classification Search .................. 600/101, 600/114, 137; 604/108, 528; 476/19, 34; 254/97, 103; 74/425
See application file for complete search history.

(56) References Cited

U.S. PATENT DOCUMENTS

| | | | | |
|---|---|---|---|---|
| 3,835,854 A | * | 9/1974 | Jewett | 604/159 |
| 6,171,234 B1 | * | 1/2001 | White et al. | 600/102 |
| 6,398,755 B1 | * | 6/2002 | Belef et al. | 604/95.01 |
| 7,582,054 B2 | * | 9/2009 | Okada | 600/106 |
| 7,615,042 B2 | | 11/2009 | Beyar et al. | 604/510 |
| 2006/0229587 A1 | | 10/2006 | Beyar et al. | |

* cited by examiner

*Primary Examiner* — Nicholas D Lucchesi
*Assistant Examiner* — Victoria P Campbell
(74) *Attorney, Agent, or Firm* — Harness, Dickey & Pierce, P.L.C.

(57) ABSTRACT

An apparatus for selectively advancing and/or rotating an elongate device, includes a carrier mounted for rotation about a primary axis and a pair of opposed rollers on the carrier adapted to drive the device in a direction along the primary axis. A mechanism drives at least one of the rollers has a first gear and a second gear. A first input selectively rotates the second gear in first or second directions to advance or retract the elongate device. A second input selectively rotates the carrier in first and second directions to rotate the elongate device. The operation of the second input alone simultaneously rotates and advances/retracts the elongate device, and the coordinated operation of the first and second inputs rotates the elongate device without advancement/retraction.

9 Claims, 10 Drawing Sheets

APPARATUS FOR SELECTIVELY ROTATING AND/OR ADVANCING AN ELONGATE DEVICE

CROSS-REFERENCE TO RELATED APPLICATIONS

This application is a continuation-in-part of U.S. patent application Ser. No. 12/196,058 filed on Aug. 21, 2008, which claims the benefit of U.S. Provisional Application No. 60/957,008, filed on Aug. 21, 2007. The entire disclosures of each of the above applications are incorporated herein by reference.

FIELD

The present disclosure relates to an apparatus for selectively rotating and/or advancing or retracting an elongate device, such as a medical catheter or guidewire.

BACKGROUND

This section provides background information related to the present disclosure which is not necessarily prior art. In many medical procedures it is common to advance an elongate device such as a catheter or guidewire into the body. In at least some of these procedures, it can also be desirable to rotate the device as well. Generally this is accomplished by the physician or other health care professional grasping the proximal portion of the device and pushing, pulling, and/or twisting. While effective, this method does not permit precise control, and the person manipulating the device can easily fatigue. Furthermore, this method often exposes the physician or healthcare professional to radiation from the imaging systems used to monitor the procedure.

Attempts have been made to provide an advancer for automatically advancing medical devices. See, for example, U.S. Pat. No. 7,276,044 for System And Methods For Advancing A Catheter; U.S. Published Application No. 2008/0045892 for System And Methods For Advancing A Catheter; Published Application No. 2006/0041245 for Systems And Methods For Medical Device Advancement And Rotation; U.S. Published Application No. US2007/0149946 for Advancer System For Coaxial Medical Devices, the entire disclosures of which are incorporated herein by reference. However a simple, reliable device that is capable of selectively advancing, retracting and rotating a device has not been previously available.

SUMMARY

This section provides a general summary of the disclosure, and is not a comprehensive disclosure of its full scope or all of its features. Embodiments of the present invention provide an apparatus for selectively advancing, retracting, and rotating an elongate device such as a catheter or guidewire. A preferred embodiment of the apparatus comprises a carrier having a pair of opposed rollers adapted to receive and engage an elongate device between them, and a drive bevel gear rotatably coupled to at least one roller, for advancing or retracting the elongate device in a direction along a primary axis. The preferred embodiment includes a first ring gear coupled to the carrier for rotating the carrier, a beveled gear that rotatably engages the drive bevel gear on the carrier, and a second ring gear coupled to the beveled gear for rotating the beveled gear. The preferred embodiment further includes a drive shaft having a plurality of drive gears thereon, the drive shaft being moveable to a first position in which only a first drive gear engages the first ring gear to permit the rotation of both the carrier having rollers engaging the elongate device and the drive bevel gear that drives at least one roller engaging the device, to thereby advance the device while rotating the device about its axis. The drive shaft is moveable to a second position in which only a second drive gear engages the second ring gear for rotating the beveled gear to permit the rotation of the drive bevel gear on the carrier that drives the roller engaging the device, to thereby advance the device without rotating the device. The drive shaft is moveable to a third position in which a third and fourth drive gear respectively engage the first ring gear and the second ring gear, to cause a rotation at the same speed of both the beveled gear and the carrier so that the carrier does not rotate relative to the beveled gear, and rotation of the carrier rotates the device without advancing the device.

The linear positioning of drive shaft and engagement of one or more drive gears permits the simultaneous rotation of the first and/or second ring gear to allow a device received between the opposing rollers to be rotated with or without advancement, or to be advance with or without rotation, such that the device can be advanced at a selected rate and/or in a desired rotational direction, by rotation of a single drive shaft.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
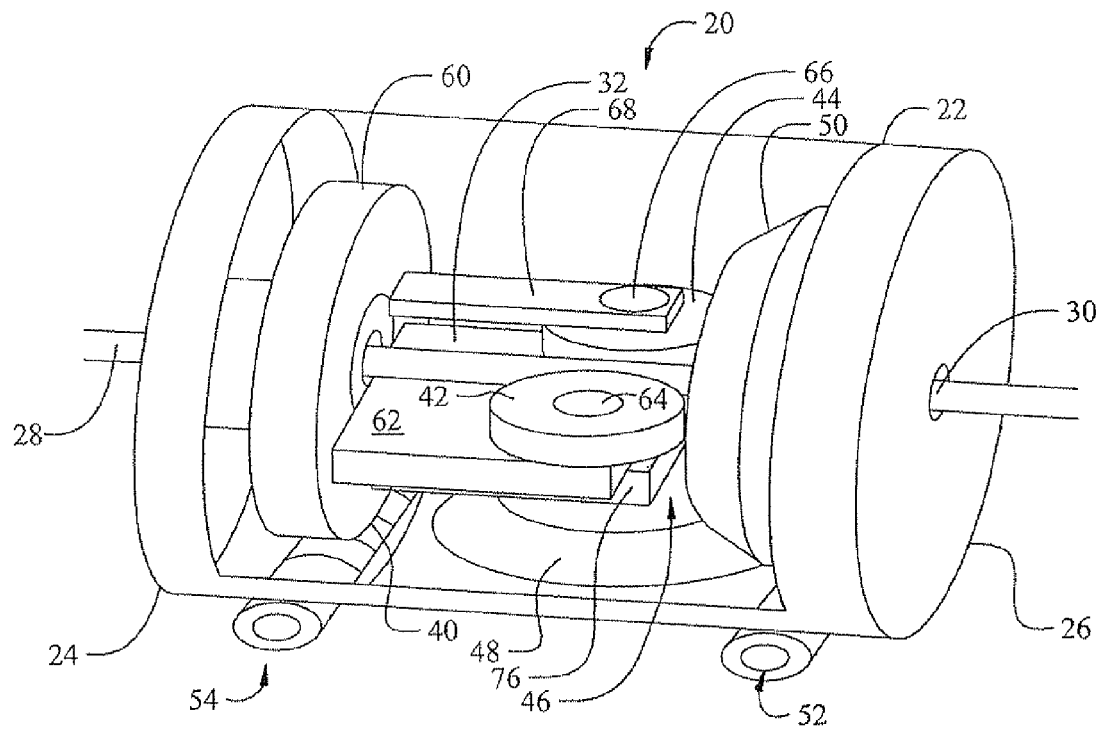
FIG. 1 is a perspective view of a preferred embodiment of an advancer constructed according to the principles of this invention.
Figure 2:
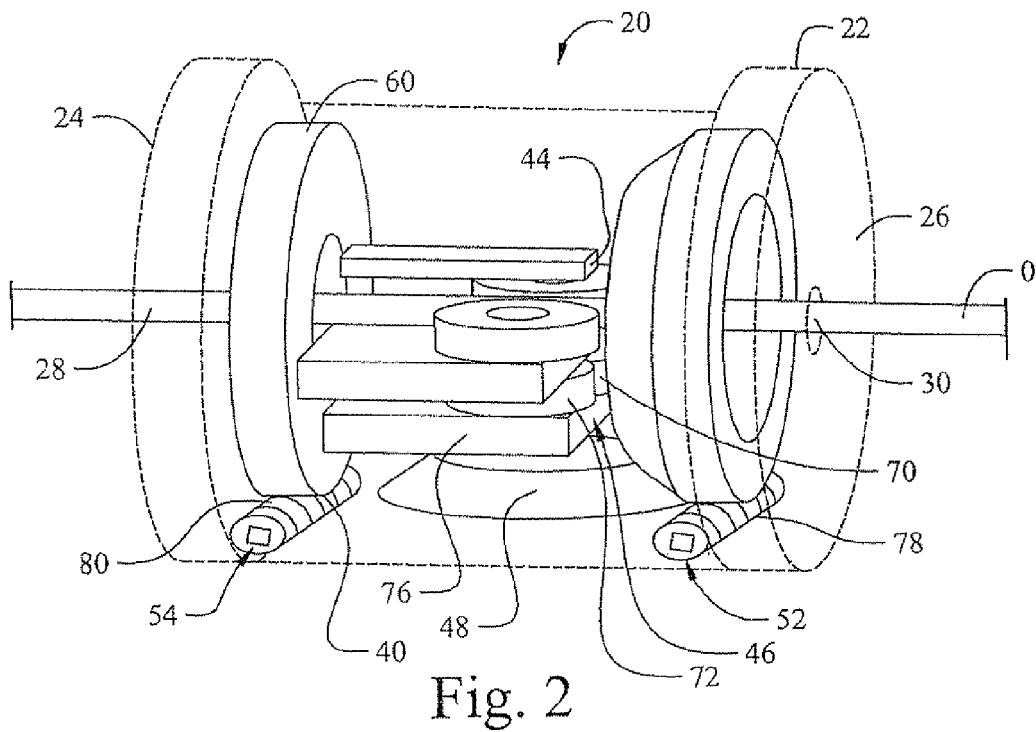
FIG. 2 is a perspective view of the preferred embodiment from a different vantage point than FIG. 1.
Figure 3:
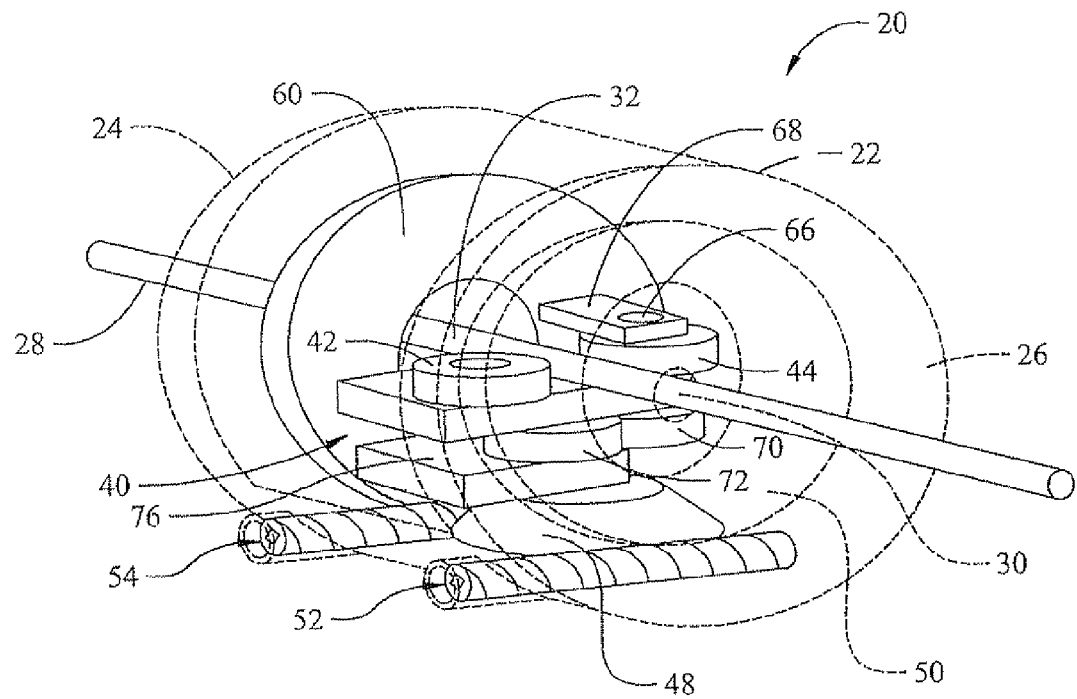
FIG. 3 is a perspective view of the preferred embodiment from a different vantage point than FIGS. 1 and 2.
Figure 4:
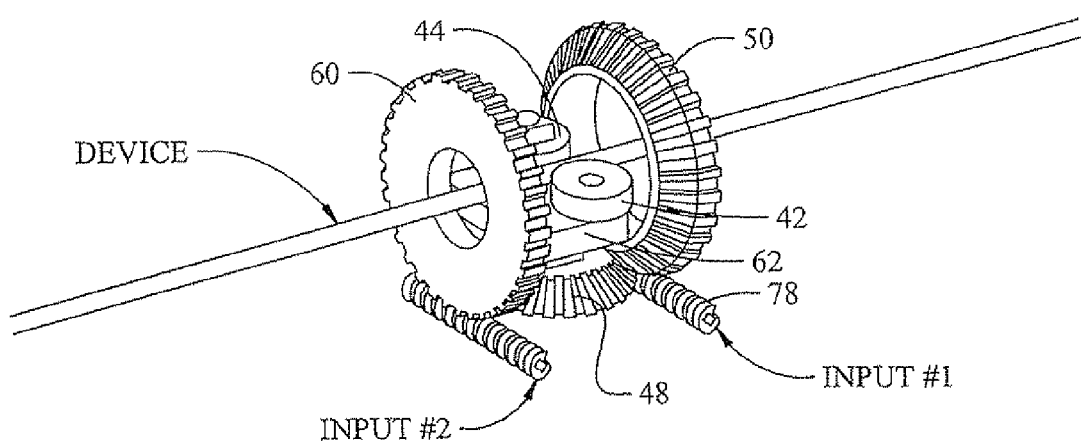
FIG. 4 is a perspective view of a second embodiment of an advancer constructed according to the principles of this invention.
Figure 5:
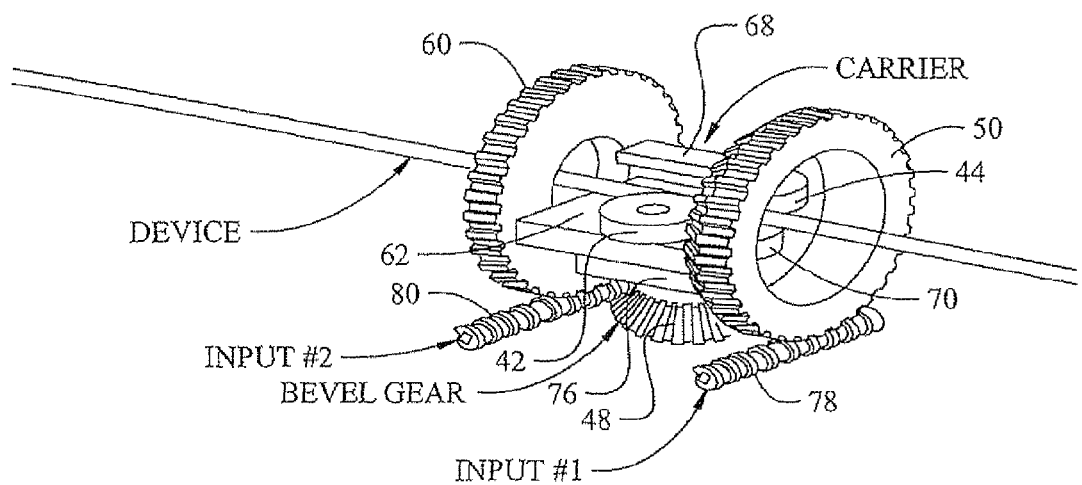
FIG. 5 is a perspective view of the second embodiment from a different vantage point than FIG. 1.
Figure 6:
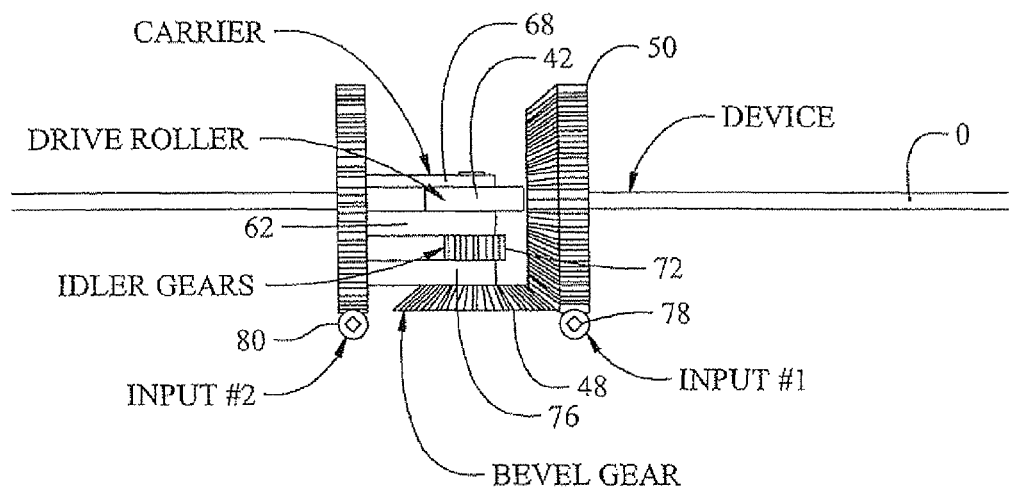
FIG. 6 is a side elevation view of the second embodiment.
Figure 7:
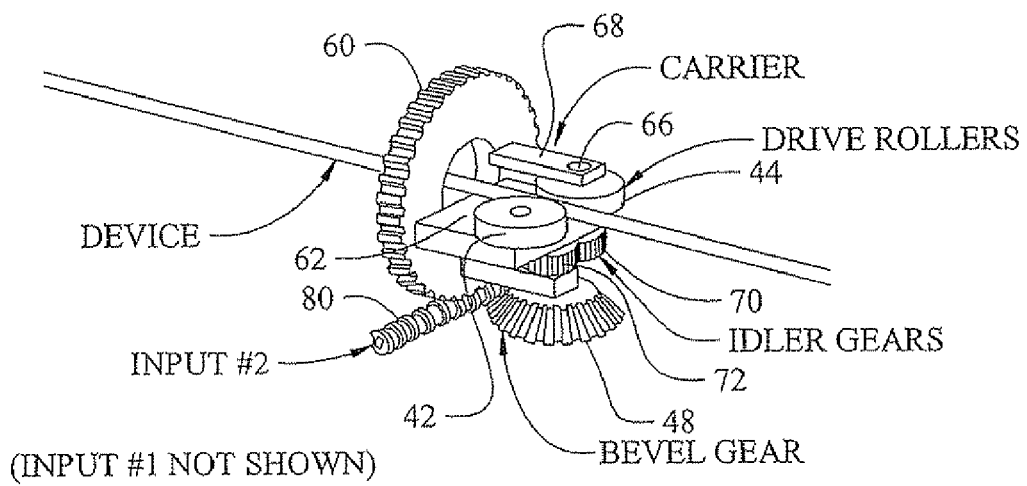
FIG. 7 is a perspective view of the second embodiment similar to FIG. 5, with portions removed to reveal details of construction.
Figure 8:
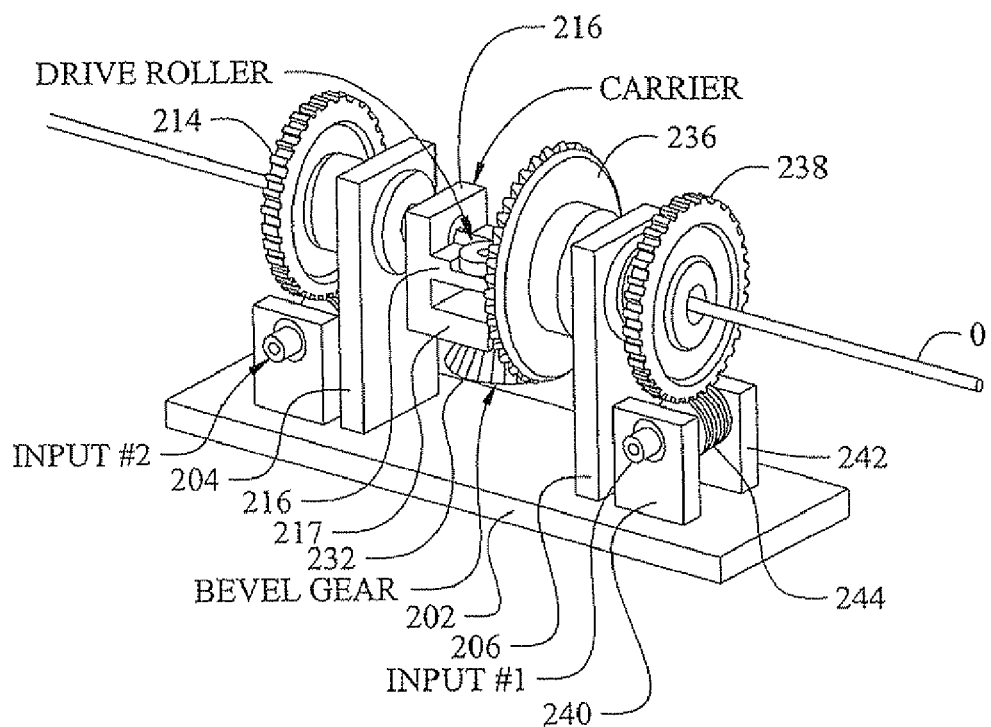
FIG. 8 is a perspective view of a third embodiment of an advancer constructed according to the principles of this invention.
Figure 9:
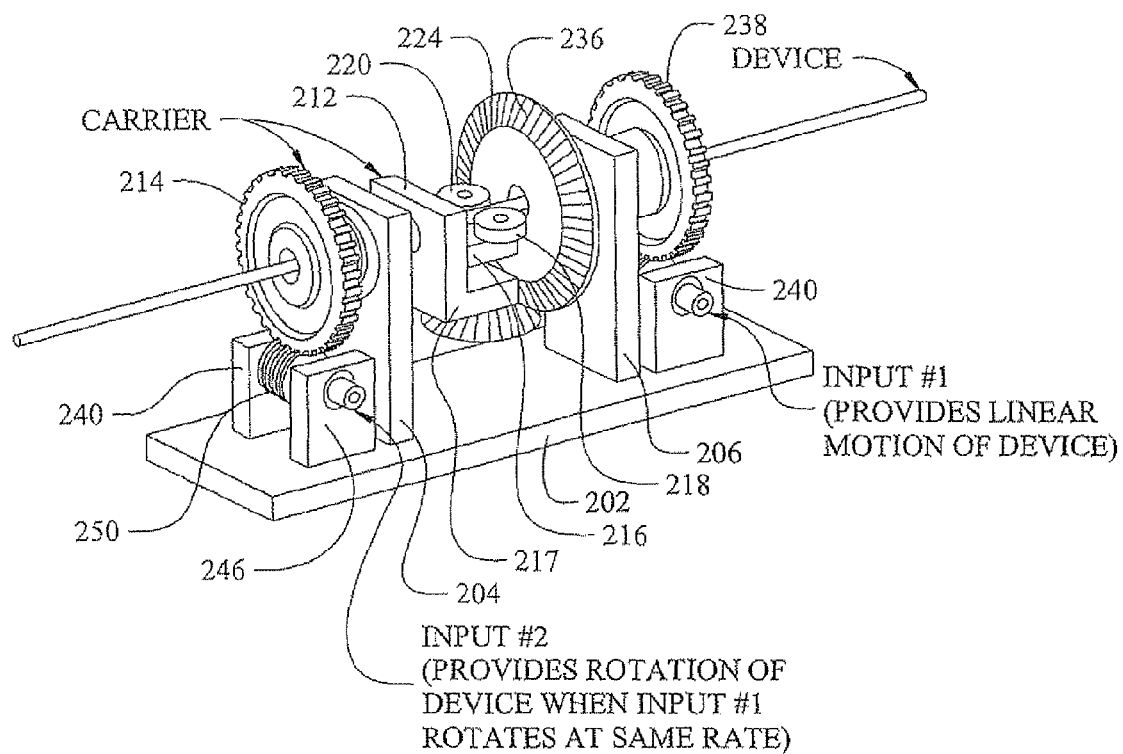
FIG. 9 is a perspective view of the third embodiment from a different vantage point than FIG. 8.
Figure 10:
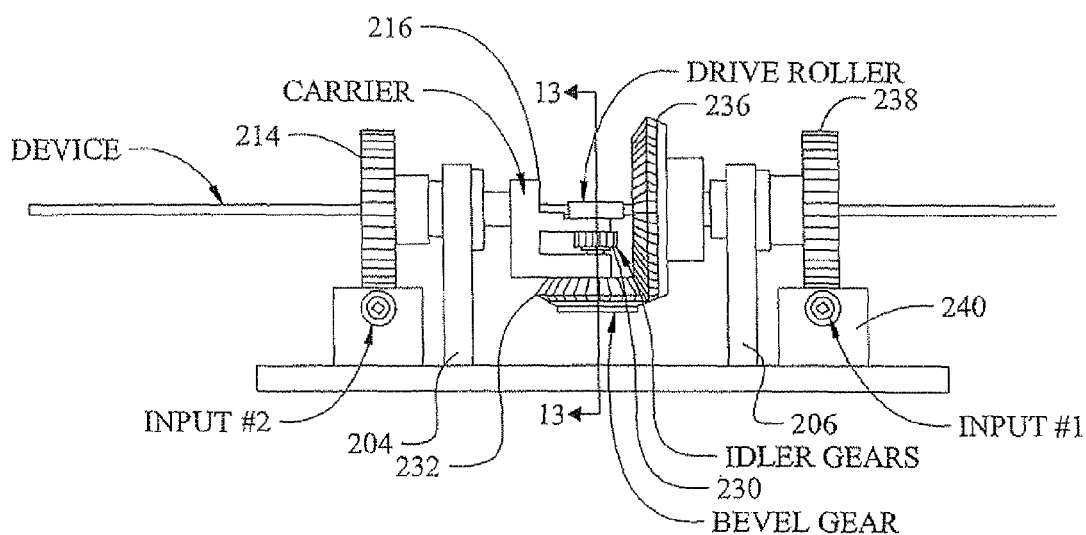
FIG. 10 is a side elevation view of the third embodiment.
Figure 11:
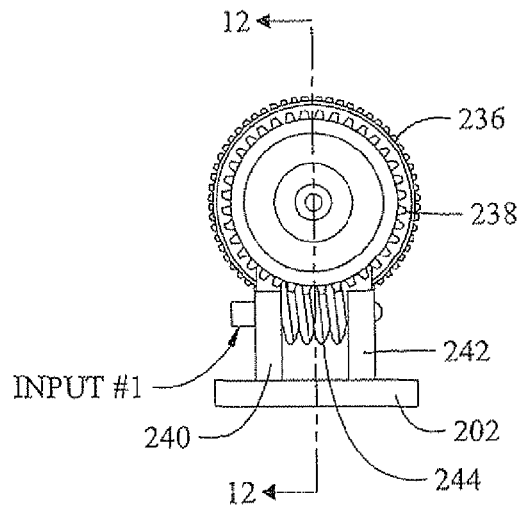
FIG. 11 is an end elevation view of the third embodiment.
Figure 12:
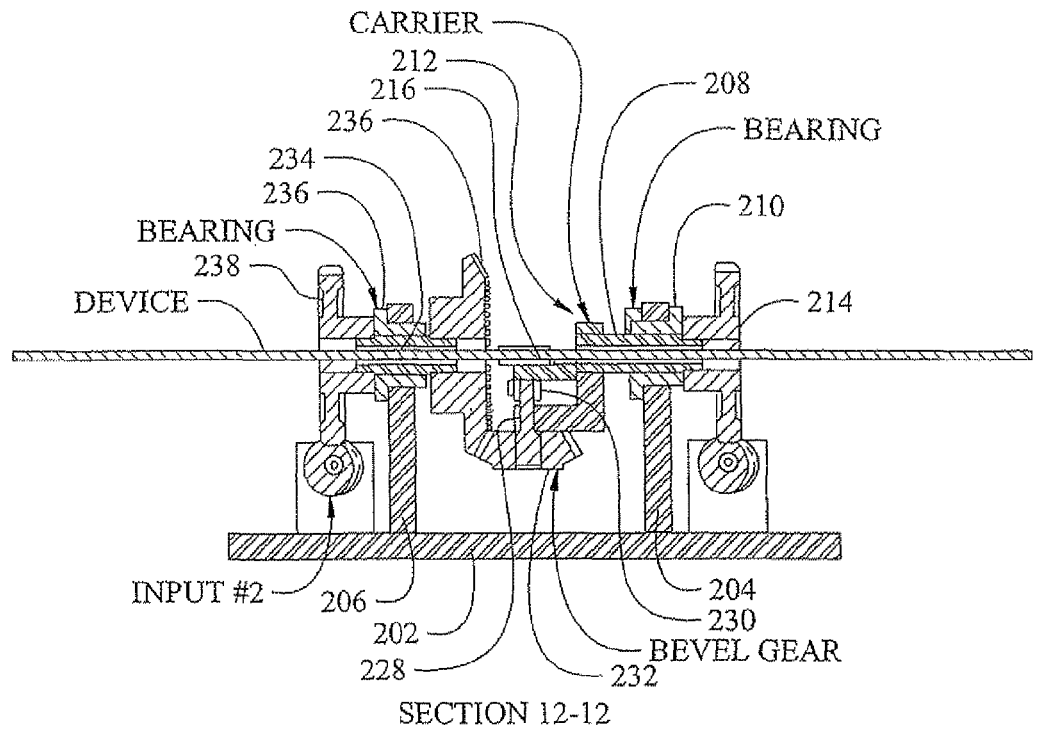
FIG. 12 is a vertical transverse cross sectional view of the third embodiment, taken along the plane of line 12-12 in FIG. 11.
Figure 13:
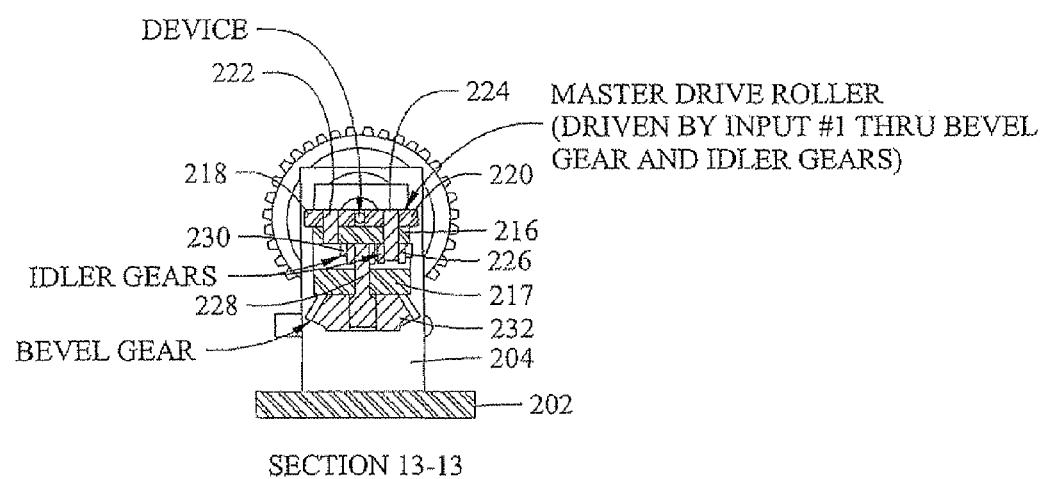
FIG. 13 is a vertical longitudinal cross sectional view of the third embodiment, taken along the plane of line 13-13 is FIG. 10.

A preferred embodiment of an apparatus for selectively rotating and/or advancing an elongate device is indicated generally as 20 in FIGS. 1-3. As shown in FIGS. 1-3 the apparatus 20 comprises a generally cylindrical housing 22, having first and second generally circular ends 24 and 26. There is an inlet 28 in the first end 24, and an outlet 30 in the second end 26, connected by a device path 32, so that an elongate device D can be inserted into the inlet 28, along the path 32, and out the outlet 30. This device D may be, for example, a medical catheter or medical guidewire. The apparatus 20 is adapted for selectively rotating and/or advancing or retracting the device D inserted therein.

The apparatus 20 comprises a carrier 40 mounted for rotation about a primary axis that is preferably aligned with the device path 32. A pair of opposed rollers 42 and 44 are mounted on the carrier 40, and are adapted to receive and engage the device D between them, and drive the device in a direction along device path 32 and the primary axis.

A drive mechanism 46 is provided for driving at least one of the pair of opposed rollers 42, 44. The drive mechanism 46 preferably comprises a first gear 48 pivotally mounted about a first axis perpendicular to the primary axis, and a second gear 50 engaging the first gear, rotatably mounted about an axis parallel to the primary axis. As shown in FIGS. 1-3 the device path extends through the second gear 50

A first input 52 is provided for selectively rotating the second gear 50 in first or second directions to advance or retract an elongate device D engaged by the pair of opposed rollers 42, 44. A second input 54 is provided for selectively rotating the carrier 40 in first and second directions to rotate an elongate device D engaged by the pair of opposed rollers 42, 44. The operation of the second input 54 alone simultaneously rotates and advances or retracts the elongate device D, because as the carrier 40 rotates rotating the device D, the first gear 48 is rotated by virtue of its engagement with second gear 50. This rotation of the first gear 48 drives at least one of the rollers 42, 44 causing the device D to advance or retract, depending on the direction that first gear 48 turns. The coordinated operation of the first and second inputs 52 and 54 allowing rotation of the elongate device D without advancement or retraction of the elongate device, by accommodating the rotation of the first gear 48 as the carrier 40 rotates.

As shown in FIGS. 1-3 in the preferred embodiment, the carrier 40 comprises a ring gear 60, with a platform 62 projecting from one side thereof, offset from the device path 32 and the primary axis. The rollers 42 and 44 are mounted on the platform 62. In this preferred embodiment, roller 42 is a slave drive roller that freely rotates on a spindle 64 projecting from the platform 60. Roller 44 is a master drive roller that is mounted on a portion of a spindle 66 that is mounted between the platform 62 and an arbor 68 also projecting from the side of the ring gear. An idler gear 70 is mounted on a portion of the spindle 66 extending through the other side of the platform 60. Another idler gear 72 is mounted on a spindle 74 rotatably mounted on an arbor 76 extending from the side of the ring gear 60. The first gear 48 is mounted on the portion of the spindle 74 extending on the other side of the arbor 76. Thus rotation of the first gear 48 turns idler gear 72 (which is mounted on the same spindle), which turns idler gear 70. The rotation of idler gear 70 turns master drive roller 44 (which is mounted on the same spindle).

The first gear 48 and the second gear 50, preferably have mating beveled faces.

The first input 52 preferably comprises a worm gear 78, which when rotated causes the second gear 50 to turn, turning the first gear 48, which turns the idler roller 72, which turns the idler roller 70, which turns the master drive roller 44.

The second input 54 preferably also comprises a worm gear 80, which when rotated causes the ring gear 60 to turn, rotating the entire carrier, which as noted above also causes the first gear 48 to turn as it moves relative to the stationary second gear 50. Thus turning of the first gear 48 will advance or retract a device D engaged by the rollers 42, 44, unless counteracted by contrary rolling of the second gear 50 by operation of the first input.

A second embodiment of an apparatus constructed according to the principles of this invention is indicated generally as 100 in FIGS. 4-7. This second embodiment is similar in construction to the first embodiment, and corresponding parts are identified by corresponding reference numerals.

As shown in FIGS. 4-7, the turning of the worm gear 78 causes the second gear 50 to turn, which causes the first gear 48 to turn, which causes idler gear 72 to turn, which causes idler gear 70 to turn, which causes master drive roller 44 to turn. The turning of master drive roller 44 causes a device D engaged between the master drive roller 44 and the slave drive roller 42 to advance or retract, depending on the direction that master drive roller 44 turns.

The turning of the worm gear 80 causes the ring gear 60 turn, which turns the platform 62. The rotation of the platform 62 causes a device D engaged by the rollers 42, 44 on the platform to turn. The rotation of the platform 62 also causes the first gear 48 to turn as it is rotated by the moving platform 62 relative to the stationary second gear 50. This rotation of the second gear 48 causes a device D engaged by the rollers 42, 44 to advance or retract (depending on the direction of rotation). Thus operation of the worm gear 80 alone causes a simultaneous rotation and advancement (or retraction) of a device D engaged by the rollers 42, 44. Through the coordinated operation of the worm gears 78 and 80 it is possible to rotate a device D and control the advancement direction and speed, without advancement or retraction, simply by operating worm gear 78 in a direction and at a speed sufficient to counteract the advancement (or retraction) of the device caused by the operation of the worm gear 80.

A third embodiment of an apparatus constructed according to the principles of this invention is indicated generally as 200 in FIGS. 8-13. This third embodiment is similar in construction to the first embodiment and second embodiments.

As shown in FIGS. 8-13, the apparatus 200 comprises a base 202, with first and second opposed perpendicularly extending first and second brackets 204 and 206. A hollow shaft 208 is mounted in a bearing 210 in an opening in bracket 204. A carrier 212 is mounted on one end of the shaft 208, and a ring gear 214 is mounted on the other end of the shaft. The carrier 212 comprises a first platform 216 on which a slave drive roller 218 and a master drive roller 220 are mounted on spindles 222 and 224, respectively. The carrier 212 also comprises a second platform 217 parallel to, but spaced from the first platform 216. The spindle 224 on which the master drive roller 220 is mounted extends through the platform 216. An idler gear 226 is mounted on the end of the spindle 224 extending through the platform 216.

A spindle 228 is rotatably mounted in the platform 217. A idler gear 230 is mounted on the spindle 228, and engages the idler gear 226. A bevel gear 232 is also mounted on the spindle 228, on the opposite side of platform 217 from the idler gear 230.

A hollow shaft 234 is mounted in a bearing 235 in an opening in bracket 206. A bevel gear 236 is mounted on one end of the shaft 234, in engagement with the bevel gear 232. A ring gear 238 is mounted in the other end of the shaft 234.

A first input device comprising vertical brackets 240 and 242 which mount a worm gear 244, is positioned on the base 202, adjacent the ring gear 238, so that worm gear 244 can drive ring gear 238. Similarly, a second input device comprising vertical brackets 246 and 248 which mount a worm gear 250, is positioned on base 202, adjacent the ring gear 214, so that the worm gear 250 can drive the ring gear 214.

An elongate device D can extend through the ring gear 214, through the shaft 208, over the platform 216, between the slave drive roller 218 and the master drive roller 220, through the bevel gear 236, through the shaft 234 and through the ring gear 248. The first and second inputs can be operated to selectively rotate and/or advance or retract an elongate device D disposed on the device.

The worm gear 244 can be operated to turn the ring gear 238. Turning the ring gear 238 turns the shaft 234 which turns the bevel gear 236. Turning the bevel gear 236 turns the bevel gear 232, which turns idler gear 230 (on the same spindle) which turns idler gear 226. Turning the idler gear 226 turns master drive roller 220 (on the same spindle) which advances or retracts the elongate device D engaged between the slave drive roller 218 and the master drive roller 220.

The worm gear 250 can be operated to turn the ring gear 214, which turns the shaft 208 which turns the carrier 212. The rotation of the carrier 212 causes the rotation of the elongate device D, which is engaged between the rollers 218 and 220 on the platform 216. The rotation of the carrier 212 also causes the rotation of the bevel gear 232, as it moves relative to the bevel gear 236. This rotation of the bevel gear 232 causes the device D to advance or retract, depending upon the direction of the rotation of the bevel gear 232. The operation of worm gear 244 causes the device D to advance or retract, depending upon the direction of operation. The operation of worm gear 250 causes the device D to rotate and advance or retract, depending upon the direction of operation. By coordinating the direction and speed of operation, the simultaneously operation of the worm gears 244 and 250 can allow the device D to be rotated without advancement, or to allow the device D to be advanced at a rate and/or in a direction other than would normally occur from operation of worm gear 250 alone.

A fourth embodiment of an apparatus constructed according to the principles of this invention is indicated generally as 300 in FIGS. 14-19. The fourth embodiment is similar in construction to the third embodiment above. As in the third embodiment, the fourth embodiment similarly comprises a base 202 with first and second opposed perpendicularly extending first and second brackets 204 and 206, a carrier 212 mounted on one end of a shaft 208, and a ring gear 214 is mounted on the other end of the shaft, as shown in FIGS. 8-13. The carrier 212 comprises a first platform 216 on which a slave drive roller 218 and a master drive roller 220 are mounted on spindles 222 and 224, respectively. The carrier 212 also comprises a second platform 217 parallel to, but spaced from the first platform 216. The spindle 224 on which the master drive roller 220 is mounted extends through the platform 216. An idler gear 226 is mounted on the end of the spindle 224 extending through the platform 216. A spindle 228 is rotatably mounted in the platform 217. A idler gear 230 is mounted on the spindle 228, and engages the idler gear 226. A bevel gear 232 is also mounted on the spindle 228, on the opposite side of platform 217 from the idler gear 230.

Referring to FIGS. 14-19, a drive shaft 310 having a plurality of drive gears 312, 314, 316 and 318 is positioned adjacent to and linearly movable relative to the ring gear 238, so that drive gears 312 and 314 can drive ring gear 238. Similarly, the drive shaft 310 and drive gears 316 and 318 are positioned adjacent to and linearly movable relative to the ring gear 214, so that drive gears 312 and 314 can drive ring gear 214. The drive shaft 310 can be linearly moved to selectively engage drive gear 312 or 314 with ring gear 238, and also, to selectively engage drive gear 316 or 318 with ring gear 214, to selectively rotate and/or advance or retract an elongate device D disposed on the apparatus.

Figure 14:
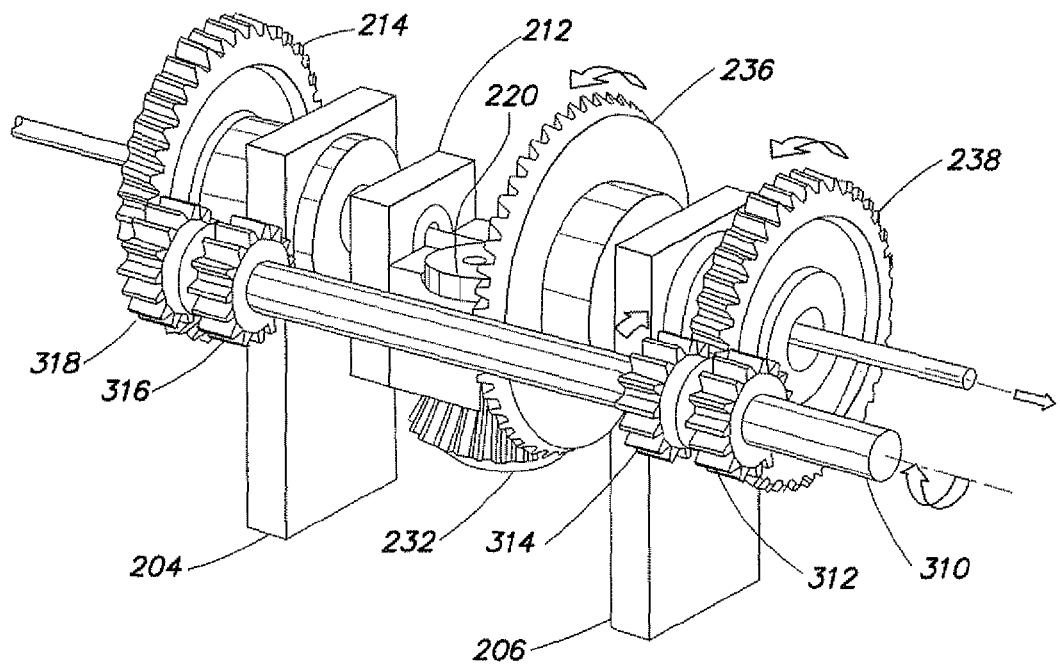
FIG. 14 is a perspective view of a fourth embodiment of an advancer constructed according to the principles of this invention.
Figure 15:
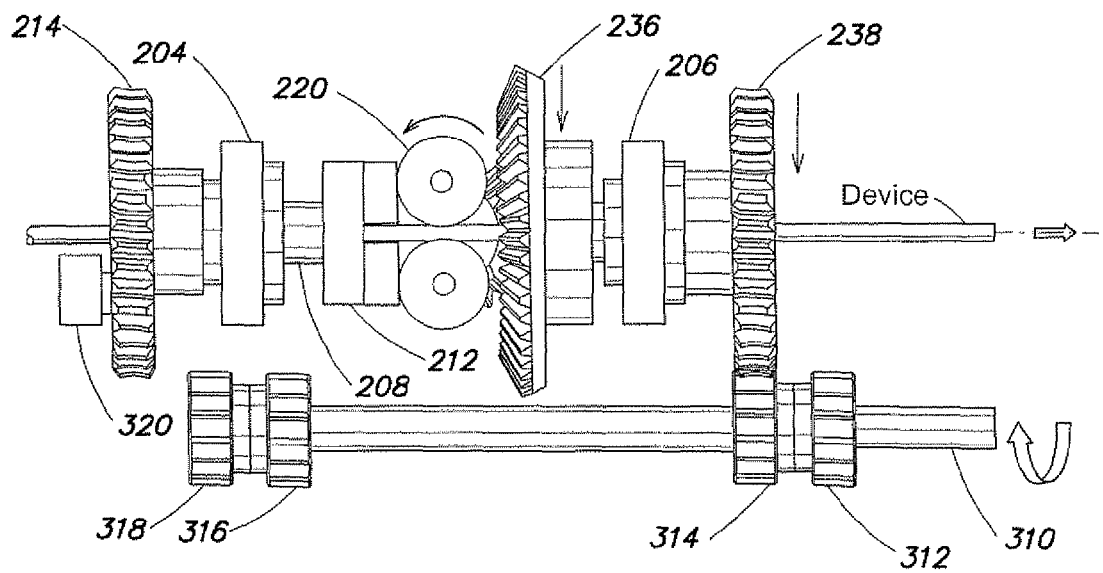
FIG. 15 is a side elevation view of the fourth embodiment.

As shown in FIGS. 14-15, the drive shaft 310 can be linearly moved to a position (shown in FIG. 15) in which drive gear 314 engages ring gear 238, while neither drive gear 316 or 318 engage ring gear 214. In this first position, rotation of the drive shaft 310 and drive gear 314 causes ring gear 238 and bevel gear 236 to rotate in the direction shown, while ring gear 214 and carrier 212 remain stationary and do not rotate. The rotation of bevel gear 236 relative to the bevel gear 232 on stationary carrier 212 causes bevel gear 232 to rotate about its axis, and in turn rotate master drive roller 220. Thus, the engagement of only drive gear 314 and ring gear 238 and rotation thereof causes rotation of master drive roller 220, to thereby advance a device adjacent the master drive roller 220, without any rotation of the device.

Figure 16:
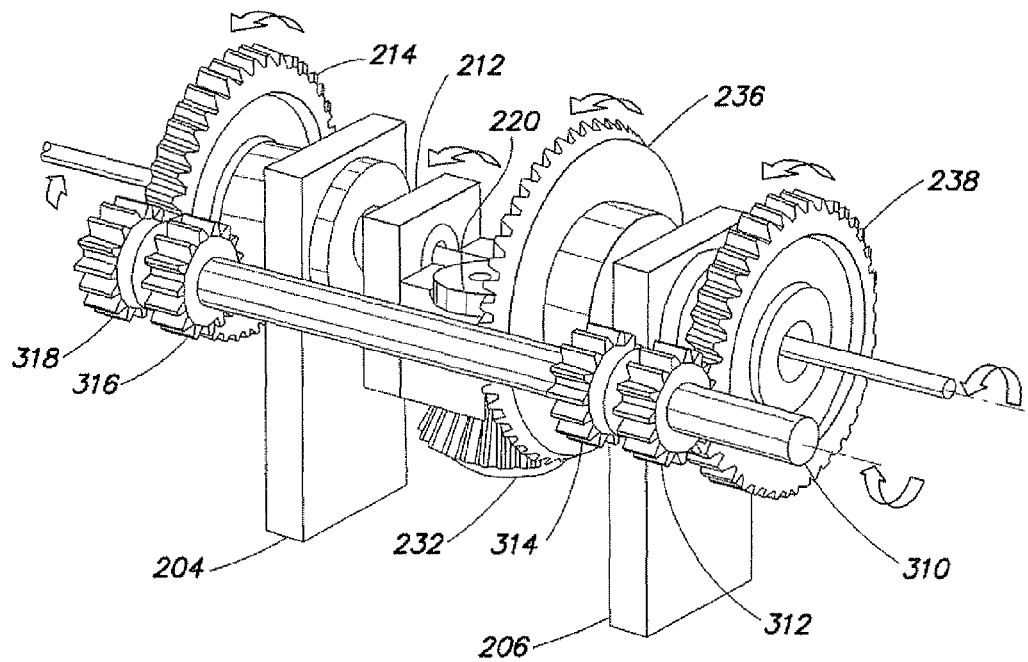
FIG. 16 is a perspective view of the fourth embodiment with one component moved to illustrate the operation of the invention.
Figure 17:
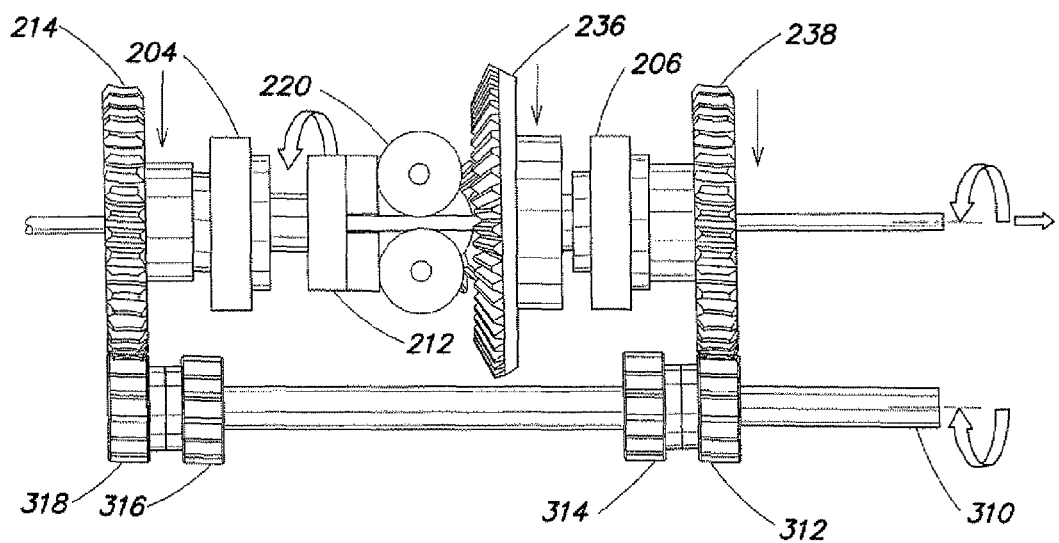
FIG. 17 is a side elevation view of the fourth embodiment in FIG. 16.

As shown in FIGS. 16-17, the drive shaft 310 can be linearly moved to a position (shown in FIG. 17) in which drive gear 318 engages ring gear 214 and drive gear 312 engages ring gear 238. In this second position, rotation of the drive shaft 310 and drive gear 318 causes ring gear 214 and carrier 212 to rotate, and causes ring gear 238 and bevel gear 236 to rotate in the direction shown. It should be noted that the gear pitch is selected such that ring gear 214 and carrier 212, as well as ring gear 238 and bevel gear 236, all rotate in the same direction as the same rotational speed (revolutions per minute). When the stationary carrier 212 with bevel gear 232 rotates at the same rotational speed as bevel gear 236, there is no rotation of bevel gear 236 relative to bevel gear 232. Thus, bevel gear 232 does not rotate about its axis or rotate master drive roller 220, such that a device adjacent the master drive roller is not advanced. However, the rotation of ring gear 214 causes the rotation of carrier 212 and the drive rollers gripping the device, and thereby causes the rotation of the device about its axis. Thus, the engagement of drive gear 318 and ring gear 214 and the engagement of drive gear 312 and ring gear 238 causes rotation of carrier 212 and rollers 220 gripping the device therebetween, to thereby rotate the device without any advancement of the device.

Figure 18:
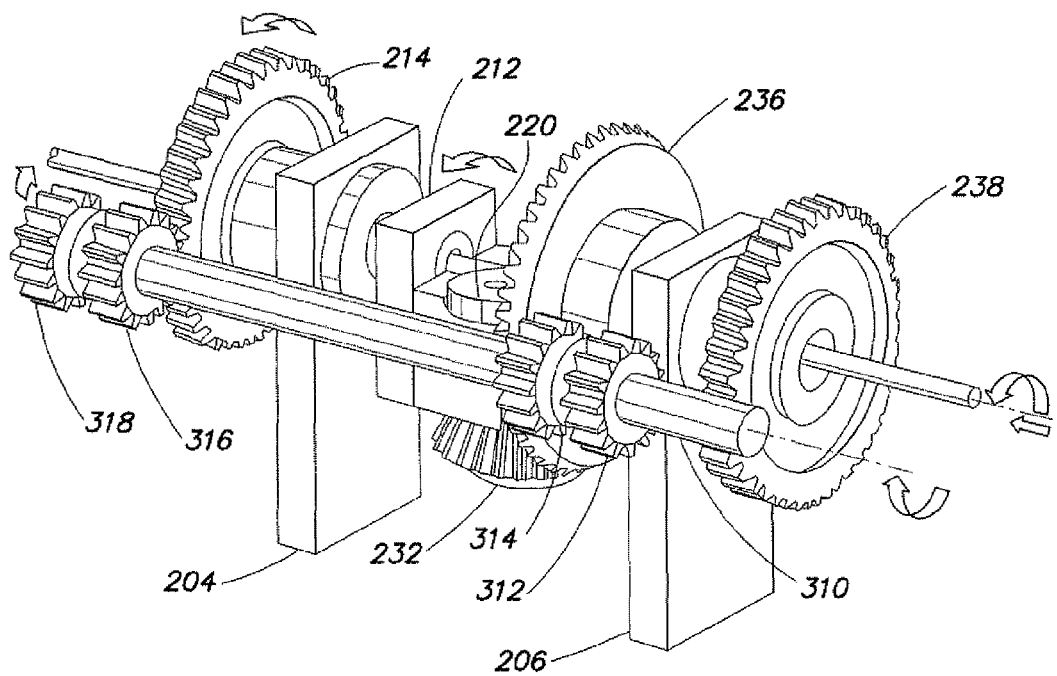
FIG. 18 is a perspective view of the fourth embodiment with one component moved to illustrate the operation of the invention.
Figure 19:
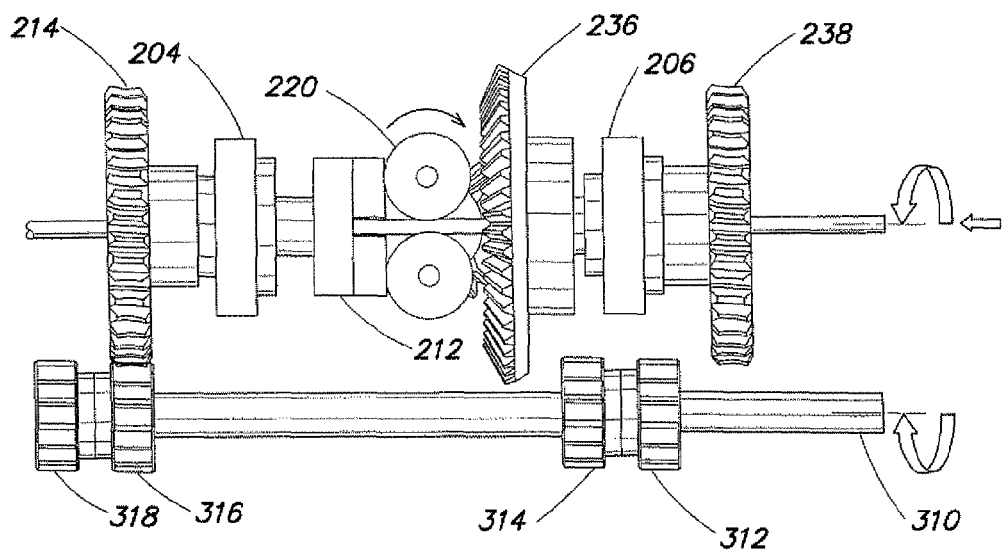
FIG. 19 is a side elevation view of the fourth embodiment in FIG. 18.

As shown in FIGS. 18-19, the drive shaft 310 can be linearly moved to a position (shown in FIG. 15) in which drive gear 316 engages ring gear 214, while neither drive gear 312 or 314 engage ring gear 238. In this third position, rotation of the drive shaft 310 and drive gear 316 causes ring gear 214 and carrier 212 to rotate in the direction shown, while ring gear 238 and bevel gear 236 remain stationary and do not rotate. The rotation of carrier 212 with bevel gear 232 relative to the stationary bevel gear 236 causes bevel gear 232 to rotate about its axis, and in turn rotate master drive roller 220.

In the third position, rotation of the drive shaft 310 and drive gear 316 causes rotation of the ring gear 214, and rotation of carrier 212 and the drive rollers gripping a device therebetween, to thereby cause the rotation of the device about its axis. Thus, the engagement of only drive gear 316 and ring gear 214 and rotation thereof causes rotation of master drive roller 220, and also causes rotation of carrier 212 and the rollers 220 gripping the device therebetween, to thereby advance the device via master drive roller 220 while also rotating the device about its axis.

The fourth embodiment accordingly includes a drive shaft having a plurality of drive gears, the drive shaft being moveable to a first position in which a first drive gear engages the first ring gear only to cause the rotation of the carrier having a roller that engages the device, and also the bevel gear on the carrier that drives the roller engaging the device, to thereby advance the device while rotating the device about its axis, the drive shaft being movable to a second position in which a second drive gear engages the second ring gear only such that the first ring gear and carrier remain stationary, to cause the rotation of the bevel gear on the carrier that drives the roller engaging the device, to thereby advance the device without rotating the device, the drive shaft being movable to a third position in which a third and fourth drive gear respectively engage the first ring gear and the second ring gear, to cause a rotation at the same speed of both the bevel gear and the carrier having the roller that engages the device, such that the carrier does not rotate relative to the bevel gear, to thereby rotate the respectively, such that rotation of the carrier having the roller engaging the device rotates the device without advancing the device.

By coordinating the linear position of drive shaft 310 and engagement of drive gears 312, 314, 316 and 318, as well as the rotational direction and speed of the drive shaft 310, the simultaneous rotation of ring gear 214 or 238 (or both ring gears 214 and 238) can allow a device D adjacent the master drive roller to be rotated with or without advancement, or to advance the device with or without rotation, such that the device D can be advanced at a selected rate and/or in a desired rotational direction, by rotation of a single drive shaft (unlike the rotation of two worm gears as in the third embodiment above). Additionally, the system may be configured to constrain the ring gears 214 and 238 from rotation when they are not engaged with a drive gear on drive shaft 310, by use of a brake or friction device 320 for engaging the ring gears 214 and 238, for example, as shown in FIG. 15. Alternatively, the motor driving the drive shaft 310 may employ a dynamic breaking phenomenon to brake motor rotation and constrain the ring gears engaging the drive shaft gears.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An apparatus for selectively advancing and/or rotating an elongate device, comprising:
   a carrier mounted for rotation about a primary axis;
   a pair of opposed rollers on the carrier adapted to receive and engage an elongate device between them, and drive the device in a direction along the primary axis;
   a drive bevel gear disposed on the carrier and coupled to a drive mechanism for driving at least one of the pair of opposed rollers on the carrier such that rotation of the drive bevel advances or retracts the elongate device;
   a first ring gear for selectively rotating a bevel gear engaged with the drive bevel gear on the carrier in first or second directions to advance or retract an elongate device engaged by the pair of opposed rollers;
   a second ring gear for selectively rotating the carrier in first and second directions to rotate an elongate device engaged by the pair of opposed rollers;
   wherein rotation of only the first ring gear rotates the drive bevel gear to advance or retract an elongate device engaged by the pair of opposed rollers, rotation of only the second ring gear rotates the carrier and causes the drive bevel gear to rotate relative to the bevel gear to simultaneously rotate an elongate device engaged by the pair of rollers and advance or retract the elongate device, and coordinated rotation of the first and second ring gears rotates the carrier to rotate an elongate device engaged by the pair of opposed rollers without advancing or retracting the elongate device; and a drive shaft having a plurality of drive gears, the drive shaft being moveable among: a first position in which one of the plurality of drive gears engages only the first ring gear to rotate only the first ring gear, to turn the bevel drive gear and advance and retract an elongate device engaged by the pair of opposed rollers; a second position in which one of the plurality of drive gears engages only the second ring gear to rotate only the second ring gear, to rotate the carrier to both rotate an elongated device engaged by the pair of opposed rollers, and move the drive bevel gear relative to the first ring gear to advance or retract the elongate device; and a third position in which one of the plurality of drive gears engages the first ring gear and another of the plurality of drive dears engages the second ring gear to simultaneously rotate the first and second ring, to rotate the carrier to both rotate an elongated device engaged by the pair of opposed rollers and move the first ring gear relative to the moving drive bevel gear so that the elongated device is not advanced or retracted as it rotates.

2. The apparatus of claim 1 wherein the bevel gear is integral with the first ring gear.

3. The apparatus of claim 1 wherein the carrier comprises a support, offset from, but parallel to, the primary axis on which the pair of opposed rollers are mounted.

4. The apparatus of claim 1 wherein the drive shaft has four drive gears, a first drive gear that engages the first ring gear when the shaft is its first position; a second drive gear that engages the second ring gear when the drive shaft is in its second position, and third and fourth drive gears that engage the first and second ring gears, respectively, when the drive shaft is in its third position.

5. The apparatus of claim 4 wherein the drive moves among its first, second and third positions by axial translation.

6. The apparatus of claim 1 wherein the drive shaft moves among its first, second and third positions by axial translation.

7. An apparatus for selectively advancing and/or rotating an elongate device, comprising:

a carrier mounted for rotation about a primary axis, comprising a support projecting parallel to, but offset from, the primary axis;

a pair of opposed rollers on the support adapted to receive and engage an elongate device between them, and to drive the elongate device in a direction along the primary axis;

a drive mechanism for driving at least one of the pair of opposed rollers, the drive mechanism including a drive bevel gear pivotally mounted on the carrier for rotation about a first axis perpendicular to the primary axis;

a first ring gear, having a beveled face for engaging the drive bevel gear, rotatably mounted about the primary axis;

a second ring gear mounted for rotation about the primary axis for rotating the carrier to rotate an elongate device engaged in the pair of opposed rollers;

a drive shaft having a plurality of drive gears, the drive shaft being moveable among: a first position in which one of the plurality of drive gears engages only the first ring gear to rotate only the first ring gear, to turn the bevel drive gear and advance and retract an elongate device engaged by the pair of opposed rollers; a second position in which one of the plurality of drive gears engages only the second ring gear to rotate only the second ring gear, to rotate the carrier to both rotate an elongated device engaged by the pair of opposed rollers, and move the drive bevel gear relative to the first ring gear to advance or retract the elongate device; and a third position in which one of the plurality of drive gears engages the first ring gear and another of the plurality of drive gears engages the second ring gear to simultaneously rotate the first and second ring, to rotate the carrier to both rotate an elongated device engaged by the pair of opposed rollers and move the first ring gear relative to the moving drive bevel gear so that the elongated device is not advanced or retracted as it rotates.

8. The apparatus of claim 7 wherein the primary axis and the path of the elongate device extend through the first ring gear.

9. The apparatus of claim 7 wherein the drive shaft has four drive gears, a first drive gear that engages the first ring gear when the shaft is its first position; a second drive gear that engages the second ring gear when the drive shaft is in its second position, and third and fourth drive gears that engage the first and second ring gears, respectively, when the drive shaft is in its third position.

* * * * *